(12) United States Patent
Neel et al.

(10) Patent No.: US 9,927,387 B2
(45) Date of Patent: Mar. 27, 2018

(54) EMBEDDED STRIP LOT AUTOCALIBRATION

(71) Applicant: Trividia Health, Inc., Fort Lauderdale, FL (US)

(72) Inventors: Gary T. Neel, Weston, FL (US); Brent E. Modzelewski, Boca Raton, FL (US); Allan Javier Caban, Lakeworth, FL (US); Adam Mark Will, Boynton Beach, FL (US); Carlos Oti, Plantation, FL (US)

(73) Assignee: Trividia Health, Inc., Fort Lauderdale, FL (US)

(*) Notice: Subject to any disclaimer, the term of this patent is extended or adjusted under 35 U.S.C. 154(b) by 238 days.

(21) Appl. No.: 14/636,463

(22) Filed: Mar. 3, 2015

(65) Prior Publication Data

US 2015/0168335 A1    Jun. 18, 2015

Related U.S. Application Data

(63) Continuation of application No. 12/115,770, filed on May 6, 2008, now Pat. No. 8,999,125, which is a continuation-in-part of application No. 11/181,778, filed on Jul. 15, 2005, now Pat. No. 9,012,232.

(51) Int. Cl.
*G01N 27/327* (2006.01)
*G01N 33/487* (2006.01)
*C12Q 1/54* (2006.01)
*G01N 35/00* (2006.01)

(52) U.S. Cl.
CPC ..... *G01N 27/327* (2013.01); *G01N 33/48771* (2013.01); *C12Q 1/54* (2013.01); *G01N 27/3272* (2013.01); *G01N 2035/00851* (2013.01); *Y10T 29/49117* (2015.01); *Y10T 29/49155* (2015.01)

(58) Field of Classification Search
CPC ........... G01N 27/3272; G01N 27/3273; G01N 33/48771
See application file for complete search history.

(56) References Cited

U.S. PATENT DOCUMENTS

| | | |
|---|---|---|
| 3,907,503 A | 9/1975 | Betts et al. |
| 3,964,871 A | 6/1976 | Hochstrasser |
| 4,059,407 A | 11/1977 | Hochstrasser |

(Continued)

FOREIGN PATENT DOCUMENTS

| | | |
|---|---|---|
| DE | 10 222 271 | 6/2003 |
| EP | 1 288 653 | 3/2003 |

(Continued)

OTHER PUBLICATIONS

JEDEC explanation of "VSS", downloaded on Apr. 26 from https://www.jedec.org/standards-documents/dictionary/terms/ground-reference-or-source-power-voltage-pin-vss-gnd.*

(Continued)

*Primary Examiner* — Alexander S Noguerola
(74) *Attorney, Agent, or Firm* — Greenberg Traurig, LLP; David J. Dykeman; Roman Fayerberg

(57) ABSTRACT

An auto-calibration system for diagnostic test strips is described for presenting data individually carried on each test strip readable by a diagnostic meter. The test strip meter may provide a predetermined varying resistance on one strip or a plurality of varying resistances from strip lot to strip lot.

13 Claims, 12 Drawing Sheets

(56) References Cited

U.S. PATENT DOCUMENTS

| | | | |
|---|---|---|---|
| 4,218,421 A | 8/1980 | Mack et al. | |
| 4,590,327 A | 5/1986 | Nath et al. | |
| 4,615,462 A | 10/1986 | Sacherer et al. | |
| 4,627,445 A | 12/1986 | Garcia et al. | |
| 4,637,403 A | 1/1987 | Garcia et al. | |
| 4,690,801 A | 9/1987 | Anderson | |
| 4,714,874 A | 12/1987 | Morris et al. | |
| 4,717,018 A | 1/1988 | Sacherer et al. | |
| 4,757,022 A | 7/1988 | Shults et al. | |
| 4,787,398 A | 11/1988 | Garcia et al. | |
| 4,797,256 A | 1/1989 | Watlington, IV | |
| 4,834,264 A | 5/1989 | Sacherer et al. | |
| 4,871,258 A | 10/1989 | Herpichboehm et al. | |
| 4,876,068 A | 10/1989 | Castaneda | |
| 4,877,580 A | 10/1989 | Aronwitz et al. | |
| 4,894,137 A | 1/1990 | Takizawa et al. | |
| 4,934,556 A | 6/1990 | Kleissendorf | |
| 4,995,402 A | 2/1991 | Smith et al. | |
| 5,087,556 A | 2/1992 | Ertinghausen | |
| 5,096,669 A | 3/1992 | Lauks et al. | |
| 5,104,619 A | 4/1992 | DeCastro | |
| 5,149,505 A | 9/1992 | English et al. | |
| 5,279,294 A | 1/1994 | Anderson et al. | |
| 5,281,395 A | 1/1994 | Marked et al. | |
| 5,413,764 A | 5/1995 | Haar | |
| 5,429,804 A | 7/1995 | Sayles | |
| 5,437,999 A | 8/1995 | Diebold et al. | |
| D367,109 S | 2/1996 | Ryner et al. | |
| 5,489,414 A | 2/1996 | Schreiber et al. | |
| 5,494,562 A | 2/1996 | Maley et al. | |
| 5,510,266 A | 4/1996 | Bonner et al. | |
| 5,575,403 A | 11/1996 | Charton et al. | |
| 5,589,045 A | 12/1996 | Hyodo | |
| 5,630,986 A | 5/1997 | Charlton et al. | |
| 5,645,798 A | 7/1997 | Schreiber et al. | |
| 5,695,623 A | 12/1997 | Michel et al. | |
| 5,709,838 A | 1/1998 | Porter et al. | |
| 5,727,548 A | 3/1998 | Hill et al. | |
| 5,728,352 A | 3/1998 | Poto et al. | |
| 5,736,103 A | 4/1998 | Pugh | |
| 5,738,244 A | 4/1998 | Charlton et al. | |
| 5,739,039 A | 4/1998 | Girault et al. | |
| 5,795,543 A | 8/1998 | Poto et al. | |
| 5,810,199 A | 9/1998 | Charlton et al. | |
| 5,821,399 A | 10/1998 | Zelin | |
| 5,854,074 A | 12/1998 | Charlton et al. | |
| 5,872,713 A | 2/1999 | Douglas et al. | |
| 5,904,898 A | 5/1999 | Markart | |
| 5,951,492 A | 9/1999 | Douglas et al. | |
| 5,989,917 A | 11/1999 | McAleer et al. | |
| 6,036,924 A | 3/2000 | Simons et al. | |
| 6,071,391 A | 6/2000 | Gotoh et al. | |
| 6,099,484 A | 8/2000 | Douglas et al. | |
| 6,106,780 A | 8/2000 | Douglas et al. | |
| 6,159,424 A | 12/2000 | Kauhaniemi et al. | |
| 6,168,957 B1 | 1/2001 | Matzinger et al. | |
| 6,176,119 B1 | 1/2001 | Kintzig | |
| 6,180,063 B1 | 1/2001 | Markart | |
| 6,192,891 B1 | 2/2001 | Gravel et al. | |
| 6,295,506 B1 | 9/2001 | Heinonen et al. | |
| 6,315,738 B1 | 11/2001 | Nishikawa et al. | |
| 6,319,209 B1 | 11/2001 | Kriz | |
| 6,352,514 B1 | 3/2002 | Douglas | |
| 6,377,894 B1* | 4/2002 | Deweese | G01N 33/48785 422/68.1 |
| 6,379,317 B1 | 4/2002 | Kintzig et al. | |
| 6,540,675 B2 | 4/2003 | Aceti et al. | |
| 6,544,475 B1 | 4/2003 | Douglas et al. | |
| 6,553,661 B2 | 4/2003 | Arnold et al. | |
| 6,558,897 B2 | 5/2003 | Scheuringer | |
| 6,579,690 B1 | 6/2003 | Bonnecaze et al. | |
| 6,599,406 B1* | 7/2003 | Kawanaka | C12Q 1/006 204/401 |
| 6,616,819 B1 | 9/2003 | Liamos et al. | |
| 6,662,439 B1 | 12/2003 | Bhullar | |
| 6,669,908 B2 | 12/2003 | Weyker et al. | |
| 6,682,704 B2 | 1/2004 | Bottwein et al. | |
| D487,594 S | 3/2004 | Alscher et al. | |
| 6,706,159 B2 | 3/2004 | Moerman et al. | |
| 6,743,635 B2 | 6/2004 | Neel et al. | |
| 6,770,487 B2 | 8/2004 | Crosby | |
| 6,773,671 B1* | 8/2004 | Lewis | G01N 33/521 422/169 |
| 6,793,802 B2 | 9/2004 | Lee et al. | |
| 6,814,844 B2 | 11/2004 | Bhullar et al. | |
| 6,827,829 B2 | 12/2004 | Kawanaka et al. | |
| 6,946,299 B2 | 9/2005 | Neet et al. | |
| 7,073,246 B2 | 7/2006 | Bhullar et al. | |
| 7,491,303 B2 | 2/2009 | Sakata et al. | |
| 7,604,721 B2* | 10/2009 | Groll | G01N 27/3272 204/403.01 |
| 8,999,125 B2 | 4/2015 | Neel et al. | |
| 9,012,232 B2 | 4/2015 | Neel et al. | |
| 2002/0057993 A1 | 5/2002 | Maisey et al. | |
| 2002/0130042 A1 | 9/2002 | Moerman et al. | |
| 2002/0137059 A1 | 9/2002 | Wu et al. | |
| 2002/0150501 A1 | 10/2002 | Robertson et al. | |
| 2002/0188224 A1 | 12/2002 | Roe et al. | |
| 2003/0031591 A1 | 2/2003 | Whitson et al. | |
| 2003/0031595 A1 | 2/2003 | Kirchhevel et al. | |
| 2003/0032190 A1 | 2/2003 | Brown et al. | |
| 2003/0036200 A1 | 2/2003 | Charlton | |
| 2003/0059350 A1 | 3/2003 | Sacherer | |
| 2003/0106810 A1 | 6/2003 | Douglas et al. | |
| 2003/0109777 A1 | 6/2003 | Kloepfer et al. | |
| 2003/0111357 A1 | 6/2003 | Black | |
| 2003/0129088 A1 | 7/2003 | Lee et al. | |
| 2003/0133847 A1 | 7/2003 | Hagen et al. | |
| 2003/0150724 A1 | 8/2003 | Kawanaka et al. | |
| 2003/0161762 A1 | 8/2003 | Caron et al. | |
| 2003/0175155 A1 | 9/2003 | Charlton | |
| 2003/0178302 A1 | 9/2003 | Bhullar et al. | |
| 2003/0185705 A1 | 10/2003 | Otake | |
| 2003/0185708 A1 | 10/2003 | Otake | |
| 2003/0186446 A1 | 10/2003 | Pugh | |
| 2003/0191415 A1 | 10/2003 | Moerman et al. | |
| 2003/0207454 A1 | 11/2003 | Eyster et al. | |
| 2003/0208140 A1 | 11/2003 | Pugh | |
| 2003/0211625 A1 | 11/2003 | Cohan et al. | |
| 2003/0212345 A1 | 11/2003 | McAllister et al. | |
| 2003/0219357 A1 | 11/2003 | Douglas et al. | |
| 2003/0223906 A1 | 12/2003 | McAllister et al. | |
| 2004/0007585 A1 | 1/2004 | Griffith et al. | |
| 2004/0026243 A1 | 2/2004 | Davies et al. | |
| 2004/0084307 A1 | 5/2004 | Kim et al. | |
| 2004/0158137 A1 | 8/2004 | Eppstein et al. | |
| 2004/0182703 A1* | 9/2004 | Bell | C12Q 1/006 204/403.11 |
| 2004/0200721 A1 | 10/2004 | Bhullar et al. | |
| 2004/0244151 A1 | 12/2004 | Sakata et al. | |
| 2005/0009126 A1 | 1/2005 | Andrews et al. | |
| 2005/0019953 A1 | 1/2005 | Groll | |
| 2005/0023137 A1 | 2/2005 | Bhullar et al. | |
| 2005/0143675 A1 | 6/2005 | Neel et al. | |
| 2005/0279647 A1 | 12/2005 | Beaty | |
| 2006/0189895 A1 | 8/2006 | Neel et al. | |
| 2007/0015286 A1 | 1/2007 | Neel et al. | |
| 2007/0110615 A1 | 5/2007 | Neel et al. | |
| 2008/0020452 A1 | 1/2008 | Popovich et al. | |

FOREIGN PATENT DOCUMENTS

| | | |
|---|---|---|
| EP | 1 431 758 | 6/2004 |
| EP | 1253204 | 5/2006 |
| JP | 02-266255 | 10/1990 |
| JP | 03-140858 | 6/1991 |
| JP | 05-003998 | 1/1993 |
| JP | 07-167812 | 7/1995 |
| JP | 10-332626 | 12/1998 |
| JP | 2000-19147 | 1/2000 |
| JP | 2001-311711 | 11/2001 |
| JP | 2001-356108 | 12/2001 |
| JP | 2002-156358 | 5/2002 |
| JP | 2002-529717 | 9/2002 |

(56) References Cited

FOREIGN PATENT DOCUMENTS

| | | |
|---|---|---|
| JP | 2003-149192 | 5/2003 |
| WO | 2000-28068 | 5/2000 |
| WO | 2000-33074 | 6/2000 |
| WO | 2002-00112 | 1/2002 |
| WO | 02-088739 | 11/2002 |
| WO | 03-029804 | 4/2003 |
| WO | 2004-113900 | 12/2004 |
| WO | 2005-073393 | 8/2005 |
| WO | 2005-088319 | 9/2005 |
| WO | 2007-011569 | 1/2007 |
| WO | 2007-121121 | 10/2007 |

OTHER PUBLICATIONS (Printed Article) "Roller Coaters," pp. 171-181.
(Printed Article) Bohan, M.F.J et al., "Evaluation of Pressures in Flexographic Printing."
(Product Data Sheet) Acheson, "Fast Drying, Conductive Graphite Coating."
(Product Data Sheet) Creative Materials, "Extremely Conductive Ink."
(Product Data Sheet) Gwent Electronic Materials Ltd., "Product Data for: -C2000802D2".
English Language Abstract and Translation of JP 2001-356108 (10 pages).
Meier et al., Circuitree 2000, pp. 36-42.
Partial English Language Translation of JP 05-003998 entitled "Partial Translation of JPU_1993003998", (3 pages).
SureFireTM' Digital Print Engines—two-page brochure from www.aelora.com (printed Apr. 8, 2004).
Vistaspectm, Ink Series—two-page brochure from www.aellora.com (printed Apr. 29, 2004).
International Search Report from PCT/US2006/040706 dated Mar. 8, 2007 (4 pages).
European Search Report and Opinion issued in European Patent Application No. 11164171 dated Oct. 4, 2011.
European Search Report and Opinion issued in European Patent Application No. 12158167 dated Mar. 26, 2012.
European Suplementary Search Report and Opinion Issued in European Patent Application No. 06786776 dated Aug. 7, 2013.
Final Office Action dated Jun. 3, 2011, received in U.S. Appl. No. 11/458,298, filed Jul. 18, 2006.
International Search Report and Written Opinion, PCT/US06/26736, dated May 30, 2008, 9 pages.
Japanese Office Action dated Feb. 1, 2012 issued in corresponding Japanese Application No. 2009-520876 (6 pages).
Office Action dated Dec. 24, 2009, received in U.S. Appl. No. 11/458,298, filed Jul. 18, 2006.
Office Action dated Feb. 17, 2009, filed in U.S. Appl. No. 11/458,298, filed Jul. 18, 2006.
Office Action dated Jan. 12, 2011, received in U.S. Appl. No. 11/458,298, filed Jul. 18, 2006.
Office Action dated Jan. 21, 2011, received in co-pending Australian Patent Application No. 2006270355.
Office Action dated Jun. 10, 2009, filed in U.S. Appl. No. 11/594,753, filed Nov. 9, 2006.
Office Action issued in Japanese Application No. 2008-521498 dated Apr. 14, 2011.
Office Action issued in U.S. Appl. No. 11/181,778 dated Aug. 22, 2008.
Office Action issued in U.S. Appl. No. 11/181,778 dated Feb. 24, 2009.
Office Action issued in U.S. Appl. No. 11/181,778 dated Jun. 23, 2009.
Office Action issued in U.S. Appl. No. 11/181,778 dated May 28, 2008.
Office Action issued in U.S. Appl. No. 11/458,298 dated Sep. 1, 2009.
PCT International Search Report, PCT/US2007/072123, dated Nov. 30, 2007.
PCT International Search Report, PCT/US2007/077378, dated Apr. 4, 2008.
PCT Written Opinion Issued in International Patent Application No. PCT/US2007/077378, dated Apr. 4, 2008.
Taiwan Office Action and Search Report issued in Taiwan Patent Application No. 095125894 dated Feb. 6, 2013 (English translation).
Taiwan Search Report issued in Taiwan Patent Application No. 096133234 dated Jan. 29, 2013 (English translation).
U.S. Appl. No. 12/115,770, filed May 6, 2008, by Neel et al.
U.S. Appl. No. 11/594,753, filed Nov. 9, 2006: Final Office Action dated Jan. 22, 2010.
U.S. Appl. No. 11/594,753, filed Nov. 9, 2006: Final Office Action dated Oct. 25, 2010.
U.S. Appl. No. 11/594,753, filed Nov. 9, 2006: Office Action dated May 21, 2010.
U.S. Appl. No. 12/115,770, filed May 6, 2008: Examiner's Answer to Appeal Brief dated May 29, 2012.
U.S. Appl. No. 12/115,770, filed May 6, 2008: Final Office Action dated Oct. 17, 2011.
U.S. Appl. No. 12/115,770, filed May 6, 2008: Office Action dated Apr. 27, 2011.

\* cited by examiner

EMBEDDED STRIP LOT AUTOCALIBRATION

RELATED APPLICATIONS

This application is a continuation of U.S. application Ser. No. 12/115,770, filed on May 6, 2008, which is a continuation in part of co-pending U.S. application Ser. No. 11/181,778, filed Jul. 15, 2005. The content of both applications is incorporated herein by reference in its entirety

TECHNICAL FIELD

The present invention relates to electrochemical sensors and, more particularly, to systems and methods for electrochemically sensing a particular constituent within a fluid through the use of diagnostic test strips including regions having a predetermined electrical property useful in identifying a test strip

BACKGROUND

Many industries have a commercial need to monitor the concentration of particular constituents in a fluid. The oil refining industry, wineries, and the dairy industry are examples of industries where fluid testing is routine. In the health care field, people such as diabetics, for example, have a need to monitor a particular constituent within their bodily fluids. A number of systems are available that allow people to test a body fluid, such as, blood, urine, or saliva, to conveniently monitor the level of a particular fluid constituent, such as, for example, cholesterol, proteins, and glucose. Patients suffering from diabetes, a disorder of the pancreas where insufficient insulin production prevents the proper digestion of sugar, have a need to carefully monitor their blood glucose levels on a daily basis. A number of systems that allow people to conveniently monitor their blood glucose levels are available. Such systems typically include a test strip where the user applies a blood sample and a meter that "reads" the test strip to determine the glucose level in the blood sample.

Among the various technologies available for measuring blood glucose levels, electrochemical technologies are particularly desirable because only a very small blood sample may be needed to perform the measurement. In amperometric electrochemical-based systems, the test strip typically includes a sample chamber that contains reagents, such as glucose oxidase and a mediator, and electrodes. When the user applies a blood sample to the sample chamber, the reagents react with the glucose, and the meter applies a voltage to the electrodes to cause a redox reaction. The meter measures the resulting current and calculates the glucose level based on the current. Other systems based on coulometry or voltametry are also known.

Because the test strip includes a biological reagent, every strip manufactured is not reproducible with the exact same sensitivity. Therefore, test strips are manufactured in distinct lots and data particular to that lot is often used as a signal by the meter's microprocessor to assist in accurately performing the meter calculation. The data is used to help accurately correlate the measured current with the actual glucose concentration. For example, the data could represent a numeric code that "signals" the meter's microprocessor to access and utilize a specific set of stored calibration values from an on-board memory device during calculation.

In past systems, the code particular to a specific lot of strips has been inputted into the meter manually by the user, or connected through some type of memory device (such as a ROM chip) packaged along with test strips from a single manufacturing lot. This step of manual input, or connection by the user, adds to the risk of improperly inputting the wrong code data. Such errors can lead to inaccurate measurements and an improper recording of the patient's history. Past systems have also included bar-code readable information incorporated onto individual strips. Individually imprinting a particular bar-code on each strip adds significant manufacturing costs to the strip production and requires the additional expense of a bar-code reader incorporated within the meter in order to obtain the information.

It should be emphasized that accurate measurements of concentration levels in a body fluid, such as blood, may be critical to the long-term health of many users. As a result, there is a need for a high level of reliability in the meters and test strips used to measure concentration levels in fluids. Thus, it is desirable to have a cost effective auto-calibration system for diagnostic test strips that more reliably and more accurately provides a signaling code for individual test strips.

SUMMARY

Embodiments of the application are directed to a diagnostic test strip, a diagnostic test strip meter, and a method of making a plurality of test strips that obviate one or more of the limitations and disadvantages of prior devices and methods.

In one embodiment, the application is directed to a diagnostic test strip. The test strip comprises an electrically insulating base layer, a conductive pattern formed on the base layer providing at least one electrode disposed on the base layer at a proximal region of the strip, electrical strip contacts disposed on the base layer at a distal region of the strip, conductive traces electrically connecting the electrodes to at least some of the electrical strip contacts, and a distinct distal conductive region provided distal to the electrical strip contacts comprising a predetermined electrical property (e.g. resistance). A reagent layer contacts at least a portion of at least one electrode and at least one discrete portion of electrical insulating material is disposed over at least one of the electrical strip contacts to at least partially form a distinct pattern readable to identify data particular to the test strip.

In one embodiment, the predetermined electrical property of a region on the test strip can be its resistance, which may be varied on a test strip or from strip lot to strip lot. The resistance can then be read by the meter device, and used to identify the calibration and other coefficients usable with the strip.

The resistance may be varied from strip to strip by using a different material with predetermined resistive properties on each strip. The resistance may be varied from strip lot to strip lot by using a different material with predetermined resistive properties for each strip lot. The resistance may also be varied from strip to strip or from strip lot to strip lot by using a combination of various materials having predetermined resistances. For example, a certain pattern of resistive material may be coated on regions of the conductive layer of a test strip. This pattern can be varied from strip to strip or from strip lot to strip lot to allow the test strip to have varying electrical characteristics when read by the test strip meter. The pattern can be varied by using one predetermined resistive material or using a combination of two or more resistive materials. Since the test strip may comprise a conductive layer and a resistive coating on top, the resistance of the test strip may be configured to fall anywhere between a completely conductive region (with no resistance) and a region having no conductivity (with high resistance).

In one embodiment, the strip can include one or more of the following additional features: wherein each of the at least one electrodes is individually connected to one contact in a first plurality of electrical strip contacts; wherein the conductive pattern at the distal region of the strip includes a second plurality of electrical strip contacts; wherein the first and second plurality of electrical strip contacts are positioned to form distinct groups of electrical contacts, the groups being spaced from one another, wherein the second plurality of electrical strip contacts form a discrete set of contacting pads; wherein the distinct pattern is configured by covering certain contacting pads with the electrical insulating material; wherein the insulating material comprises a non-conductive insulating ink; wherein an electrically insulating region separates the first and second plurality of electrical strip contacts; wherein the contacting pads are configured for contact, when inserted into a compatible meter, with a plurality of contacts in a corresponding connector of the meter; further comprising a grounding contacting pad configured to establish a common connection to electrical ground; wherein said grounding contacting pad is positioned on the strip proximally relative to the remaining contacting pads through a non-conductive notch portion at a distal region of the strip; wherein an additional conductive pattern is formed on the insulating layer on a side opposite from that including the first and second plurality of electrical strip contacts, the additional conductive pattern comprising a third plurality of electrical strip contacts and at least one discrete portion of electrical insulating material disposed over at least one of the third plurality of electrical strip contacts to form a distinct pattern readable to further identify data particular to the test strip; wherein the first and second plurality of electrical strip contacts are positioned to form first and second distinct rows of contacts; wherein the first and second rows of contacts are laterally staggered relative to each other; and wherein a resistive element is disposed over at least one of the electrical strip contacts to form part of the distinct pattern readable to identify data particular to the test strip.

The conductive layer in the above embodiment may be covered by a coating resistive layer having a range of resistive values. The resistive values may be configured by the use of a range of materials having resistive properties. These coating materials may include, but are not limited to: carbon, tantalum nitride (TaN), ruthenium dioxide ($RuO_2$), lead oxide (PbO), bismuth ruthenate ($Bi_2Ru_2O_7$), nickel chromium (NiCr), bismuth iridate ($Bi_2Ir_2O_7$), indium tin oxodie (ITO), palladium, and/or by a combination of these materials.

The resistance may be varied from strip to strip by using a different material with predetermined resistive properties on each strip. The resistance may be varied from strip lot to strip lot by using a different material with predetermined resistive properties for each strip lot. The resistance may also be varied from strip to strip or from strip lot to strip lot by using a combination of various materials having predetermined resistances. For example, a certain pattern of resistive material may be coated on the regions of the conductive layer of a test strip. This pattern can be varied from strip to strip or from strip lot to strip lot to allow the test strip to have various electrical characteristics when read by the test strip meter. The pattern can be varied by using one predetermined resistive material or using a combination of two or more resistive materials. Since the test strip may comprise a conductive layer and a resistive coating on top, the resistance of a sensed region of the test strip may be configured to fall anywhere between a highly conductive region (with no resistance) and a non-conductive region (with high resistance).

Another embodiment of the application is directed to a method of determining a constituent level within a fluid, comprising providing a diagnostic test device comprising at least one electrically insulating layer and a conductive pattern formed on the at least one insulating layer. The conductive pattern includes at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts. A reagent layer contacts at least a portion of at least one electrode and at least one discrete portion of electrical insulating material is disposed over at least one of the electrical strip contacts to at least partially form a distinct pattern readable to identify data particular to the test strip. The method further comprises connecting the distal region of the strip to a constituent level meter such that the electrical strip contacts engage with corresponding meter connector contacts, applying a fluid sample at the reagent layer, taking a measurement using the plurality of electrodes, identifying particular data based on the distinct pattern formed at least in part by the electrical insulating material disposed over at least one of the electrical strip contacts, and calculating the fluid constituent concentration based on the value of measured current and the identified data.

In various embodiments, the method may include one or more of the following additional features: wherein each of the plurality of electrodes are individually connected to one contact in a first plurality of electrical strip contacts; wherein the conductive pattern at a distal region of the strip includes a second plurality of electrical strip contacts individually electrically isolated to form a discrete set of contacting pads; wherein identifying particular data includes reading the distinct pattern through an analog method; wherein identifying particular data includes reading the distinct pattern through a digital method; wherein providing a diagnostic test device further comprises covering certain contacting pads with the electrical insulating material such that a high impedance path is created and identifying particular data further includes, connecting a preset resistive ladder to a predetermined number of meter connector contacts such that a particular resulting voltage drop, resistance, or current measurement, in a circuit completed through the connection of the contacting pads and corresponding meter connector contacts, signals the meter to access distinct calibration information; wherein identifying particular data includes, reading a meter connection between each contacting pad and a corresponding connector contact as either high impedance or low impedance and assigning a digital value to the connection in a circuit completed through the connection of the contacting pads and corresponding meter connector contacts such that the resulting digital value signals the meter to access distinct calibration information; wherein the number of code variations is determined by the expression $N=2^P$, where P is equal to the number of contacting pads; wherein the meter includes an auto-on/wake-up feature provided by a conductive contacting pad and the number of code variations is determined by the expression $N=2^P-1$, where P is equal to the number of contacting pads; and further comprising providing a resistive element over at least one of the electrical strip contacts to form part of the distinct pattern and wherein identifying particular calibration data includes, reading a meter connection between the resistive element and a corresponding connector contact and alerting the meter to access an additional set of data relating to the particular test strip.

Another embodiment of the invention is directed to a diagnostic test strip meter. The diagnostic test strip meter may comprise a connector region and electronics for decoding various resistance values of various test strips as identifying information. The connector is formed to mate with a region of the test strip.

Another embodiment of the invention is directed to a method of making a plurality of test strips comprising forming a plurality of test strip structures on one sheet where each of the test strip structures includes a sample chamber, an electrically insulating layer, a conductive pattern including a plurality of electrodes formed on said sheet, and a plurality of electrical strip contacts, formed on said sheet, a portion of which are electrically connected to said plurality of electrodes. The test strip structures further include a set of electrical strip contacts individually electrically isolated to form a discrete set of contacting pads formed on said sheet and electrically isolated from said plurality of electrodes and at least one discrete portion of electrical insulating material disposed over at least one of the contacting pads to at least partially form a distinct pattern readable to identify data particular to the test strip. One or more of the contacts can be formed having a predetermined electrical property, e.g. resistance, which can be measured and decoded. The method is completed by separating the test strip structures into a plurality of test strips.

The contacts, having a predetermined electrical property (e.g., resistance), may be formed using one or a combination of two or more materials have predetermined resistances. The distinct pattern on the test strip readable to identify data particular to the test strip may be formed using one or a combination of two or more materials having predetermined resistances placed in a variety of ways on the test strip surface.

In one embodiment, the method of making test strips includes making strips in lots where the electrical resistance of at least one region of a test strip can vary from lot to lot.

In another embodiment, the method of making test strips includes making strips individually where the electrical resistance of at least one region of a test strip can vary from strip to strip.

In various embodiments, the method can include the following additional feature of forming at least one contacting pad to include an auto-on electrical contact.

Another embodiment of the application is directed to a diagnostic test strip comprising at least one electrically insulating layer, a conductive pattern formed on the at least one insulating layer, the conductive pattern including at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts. A reagent layer contacts at least a portion of at least one electrode and each of the electrical strip contacts is selectively coverable with a discrete portion of electrical insulating material to at least partially form a distinct pattern readable to identify data particular to the test strip.

In various embodiments, the strip can include one or more of the following additional features: at least one discrete portion of electrical insulating material disposed over at least one of the electrical strip contacts to at least partially form a distinct pattern readable to identify data particular to the test strip; wherein the distinct pattern readable to identify data particular to the test strip comprises an arrangement where none of the electrical strip contacts are covered with electrical insulating material; wherein a resistive element is disposed over at least one of the electrical strip contacts to form part of the distinct pattern readable to identify data particular to the test strip; wherein each of the at least one electrodes is individually connected to one contact in a first plurality of electrical strip contacts; wherein the conductive pattern at the distal region of the strip includes a second plurality of electrical strip contacts; wherein the first and second plurality of electrical strip contacts are positioned to form distinct groups of electrical contacts, the groups being spaced from one another; wherein the second plurality of electrical strip contacts form a discrete set of contacting pads; wherein the insulating material comprises a non-conductive insulating ink; wherein the contacting pads are configured for contact, when inserted into a compatible meter, with a plurality of contacts in a corresponding connector of the meter.

The distinct pattern may be formed by arranging the electrical strip contacts on various regions of the test strip comprising one or more resistive coatings, one or more conductive coatings, or a combination of a resistive and conductive coatings.

Another embodiment of the invention is directed to a diagnostic test strip comprising at least one electrically insulating layer, a conductive pattern formed on the at least one insulating layer, the conductive pattern including at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts. A reagent layer contacts at least a portion of at least one electrode. The strip further includes a first plurality of electrical strip contacts comprised of contacts individually connected to an electrode, a second plurality of electrical strip contacts comprised of the conductive pattern at the distal region of the strip, and wherein an electrically insulating material separates the first and second plurality of electrical strip contacts.

The resistance may also be varied from strip to strip or from strip lot to strip lot by using a combination of various materials having predetermined resistances. For example, a certain pattern of resistive material may be coated on the conductive layer of a test strip. This pattern can be varied from strip to strip or from strip lot to strip lot to allow the test strip to have various characteristics when read by the test strip meter. The pattern can be varied by using one predetermined resistive material or using a combination of two or more resistive materials. Since the test strip may comprise a conductive layer and a resistive coating on top, the resistance of the test strip may be configured to fall anywhere between highly conductive (with no resistance) and non-conductive (with high resistance).

In various embodiments, the strip can include one or more of the following additional features: wherein each of the electrical strip contacts comprising the second plurality is selectively coverable with a discrete portion of electrical insulating material to at least partially form a distinct pattern readable to identify data particular to the test strip; at least one discrete portion of electrical insulating material disposed over at least one of the electrical strip contacts to at least partially form a distinct pattern readable to identify data particular to the test strip; wherein the distinct pattern readable to identify data particular to the test strip comprises an arrangement where none of the electrical strip contacts are covered with electrical insulating material; wherein a resistive element is disposed over at least one of the electrical strip contacts to form part of the distinct pattern readable to identify data particular to the test strip; wherein the second plurality of electrical strip contacts form a discrete set of contacting pads; wherein the insulating material comprises a non-conductive insulating ink; wherein the contacting pads are configured for contact, when inserted into a compatible meter, with a plurality of contacts in a corresponding connector of the meter.

Another embodiment of the invention is directed to a method of making a test strip comprising providing at least one electrically insulating layer, providing a conductive pattern on the at least one insulating layer, the conductive pattern including at least one electrode disposed on the at least one insulating layer at a proximal region of the strip, electrical strip contacts disposed on at least one insulating layer at a distal region of the strip, and conductive traces electrically connecting the electrodes to at least some of the electrical strip contacts, providing a reagent layer contacting at least a portion of at least one electrode, and selectively covering at least one of the electrical strip contacts with a discrete portion of electrical insulating material to at least partially form a distinct pattern readable to identify data particular to the test strip.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION

Figure 1:
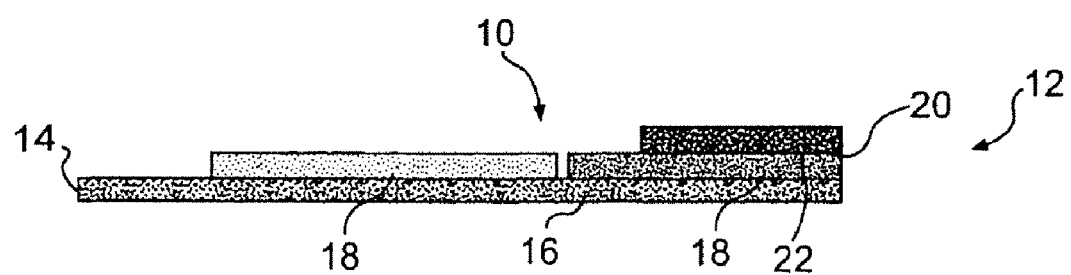
FIG. 1 is a general cross-sectional view of a test strip according to an embodiment consistent with the invention.

Reference will now be made in detail to the exemplary embodiments of the invention, examples of which are illustrated in the accompanying drawings. Wherever possible, the same reference numbers will be used throughout the drawings to refer to the same or like parts.

According to exemplary embodiments, the application relates to a system for measuring a body fluid constituent including a test strip and a meter. An individual test strip may also include an embedded code relating to data associated with a lot of test strips, or data particular to that individual strip. The embedded information presents data readable by the meter signaling the meter's microprocessor to access and utilize a specific set of stored calibration parameters particular to test strips from a manufacturing lot to which the individual strip belongs, or to an individual test strip. The system may also include a check strip that the user may insert into the meter to check that the instrument is electrically calibrated and functioning properly. For purposes of this disclosure, "distal" refers to the portion of a test strip further from the device operator during normal use and "proximal" refers to the portion closer to the device operator during normal use.

The test strip may include a sample chamber for receiving a user's fluid sample, such as, for example, a blood sample. The sample chamber and test strip of the present specification can be formed using materials and methods described in commonly owned U.S. Pat. No. 6,743,635, which is hereby incorporated by reference in its entirety. Accordingly, the sample chamber may include a first opening in the proximal end of the test strip and a second opening for venting the sample chamber. The sample chamber may be dimensioned so as to be able to draw the blood sample in through the first opening, and to hold the blood sample in the sample chamber, by capillary action. The test strip can include a tapered section that is narrowest at the proximal end, or can include other indicia in order to make it easier for the user to locate the first opening and apply the blood sample.

A working electrode and counter electrode can be disposed in the sample chamber optionally along with fill-detect electrodes. A reagent layer is disposed in the sample chamber and preferably contacts at least the working electrode. The reagent layer may include an enzyme, such as glucose oxidase, and a mediator, such as potassium ferricyanide or ruthenium hexamine. The test strip has, near its distal end, a first plurality of electrical strip contacts that are electrically connected to the electrodes via conductive traces. In addition, the test strip may also include a second plurality of electrical strip contacts near the distal end of the strip. The second plurality of electrical contacts can be arranged such that they provide, when the strip is inserted into the meter, a distinctly discernable lot code readable by the meter. As noted above, the readable code can be read as a signal to access data, such as calibration coefficients, from an on-board memory unit in the meter related to test strips from that lot, or even information corresponding to individual test strips.

The second plurality of electrical contacts may comprise a resistive coating, a conductive coating, or a combination of a resistive and conductive coating. The resistance may be varied from strip to strip or from strip lot to strip lot by using a different material with predetermined resistive properties on each strip or on each strip lot. The resistance may also be varied from strip to strip or from strip lot to strip lot by using a combination of various materials having predetermined resistances. For example, a certain pattern of resistive material may be coated on the conductive layer of a test strip. This pattern can be varied from strip to strip or from strip lot to strip lot to allow the test strip to have various characteristics when read by the test strip meter. The pattern can be varied by using one predetermined resistive material or using a combination of two or more resistive materials. Since the test strip may comprise a conductive layer and a resistive coating on top, the resistance of the sensed region of the test strip may be configured to fall anywhere between highly conductive (with no resistance) and non-conductive (with high resistance).

The meter may be battery powered and may stay in a low-power sleep mode when not in use in order to save power. When the test strip is inserted into the meter, the first and second plurality of electrical contacts on the test strip contact corresponding electrical contacts in the meter. The second plurality of electrical contacts may bridge a pair of electrical contacts in the meter, causing a current to flow through a portion of the second plurality of electrical contacts. The current flow through the second plurality of electrical contacts causes the meter to wake up and enter an active mode. The meter also reads the code information provided by the second plurality and can then identify, for example, the particular test to be performed, or a confirmation of proper operating status. In addition, the meter can also identify the inserted strip as either a test strip or a check strip based on the particular code information. If the meter detects a check strip, it performs a check strip sequence. If the meter detects a test strip, it performs a test strip sequence.

In the test strip sequence, the meter validates the working electrode, counter electrode, and, if included, the fill-detect electrodes, by confirming that there are no low-impedance paths between any of these electrodes. If the electrodes are valid, the meter indicates to the user that sample may be applied to the test strip. The meter then applies a drop-detect voltage between the working and counter electrodes and detects a fluid sample, for example, a blood sample, by detecting a current flow between the working and counter electrodes (i.e., a current flow through the blood sample as it bridges the working and counter electrodes). To detect that an adequate sample is present in the sample chamber and that the blood sample has traversed the reagent layer and mixed with the chemical constituents in the reagent layer, the meter may apply a fill-detect voltage between the fill-detect electrodes and measure any resulting current flowing between the fill-detect electrodes. If this resulting current reaches a sufficient level within a predetermined period of time, the meter indicates to the user that adequate sample is present and has mixed with the reagent layer.

In one embodiment, the test strip meter comprises a decoder for decoding a predetermined electrical property, e.g. resistance, from the test strips as information. The decoder operates with, or is a part of, a microprocessor.

The meter can be programmed to wait for a predetermined period of time after initially detecting the blood sample, to allow the blood sample to react with the reagent layer or can immediately begin taking readings in sequence. During a fluid measurement period, the meter applies an assay voltage between the working and counter electrodes and takes one or more measurements of the resulting current flowing between the working and counter electrodes. The assay voltage is near the redox potential of the chemistry in the reagent layer, and the resulting current is related to the concentration of the particular constituent measured, such as, for example, the glucose level in a blood sample.

In one example, the reagent layer may react with glucose in the blood sample in order to determine the particular glucose concentration. In one example, glucose oxidase is used in the reagent layer. The recitation of glucose oxidase is intended as an example only and other materials can be used without departing from the scope of the invention. Other possible mediators include, but are not limited to, ruthenium and osmium. During a sample test, the glucose oxidase initiates a reaction that oxidizes the glucose to gluconic acid and reduces the ferricyanide to ferrocyanide. When an appropriate voltage is applied to a working electrode, relative to a counter electrode, the ferrocyanide is oxidized to ferricyanide, thereby generating a current that is related to the glucose concentration in the blood sample. The meter then calculates the glucose level based on the measured current and on calibration data that the meter has been signaled to access by the code data read from the second plurality of electrical contacts associated with the test strip. The meter then displays the calculated glucose level to the user. Each of the above-described components and their interconnection will now be described.

FIG. 1 illustrates a general cross-sectional view of an embodiment of a test strip 10. Test strip 10 includes a proximal connecting end 12, a distal end 14, and is formed with a base layer 16 extending along the entire length of test strip 10. Base layer 16 is preferably composed of an electrically insulating material and has a thickness sufficient to provide structural support to test strip 10. For purposes of this application, an insulating material (e.g. an insulating layer, coating, ink, or substrate etc.) comprises any material in which electrons or ions cannot be moved easily, hence preventing the flow of electric current. Accordingly, an element can be said to be insulated when it is separated from other conducting surfaces by a dielectric substance or air space permanently offering a high resistance to the passage of current and to disruptive discharge through the substance or space. By contrast, for purposes of this application, a resistive element, is one that introduces an increased level of impedance into a circuit that reduces (but does not necessarily prevent) the flow of electric current. Base layer 16, for example, may be polyester that is about 0.014 inches thick, although other sizes may be used depending on the particular application and manufacturing method. Disposed on base layer 16 is a conductive pattern (not shown) with a predetermined resistance.

The conductive pattern includes a plurality of electrodes disposed on base layer 16 near proximal end 12, a plurality of electrical strip contacts disposed on base layer 16 near distal end 14, and a plurality of conductive traces electrically connecting the electrodes to the plurality of electrical strip contacts. For purposes of this application, the noun "contact" denotes an area intended for mechanical engagement with another corresponding "contact" irrespective of whether an electric circuit is completed, or passes through the particular area.

In one embodiment, the plurality of electrodes may include a working electrode, a counter electrode, and fill-detect electrodes. The conductive pattern may be applied by applying a conductive material onto base layer 16. The conductive pattern can be applied to the top side of the strip, the bottom side of the strip, or a combination of both. The electrode material may be provided by thin film vacuum sputtering of a conductive material (e.g. Gold) and a semi-conductive material (e.g. Indium Zinc Oxide) onto the base layer 16. The resulting electrode layer can then be further patterned according to the specific application by forming particular conductive regions/pathways through a laser ablation process. Alternative materials and methods for providing a conductive pattern in addition to screen printing can be employed without departing from the scope of the invention.

A dielectric insulating layer 18 can be formed over the conductive pattern along a portion of the test strip between the measuring electrodes and the plurality of electrical strip contacts in order to prevent scratching, and other damage, to the electrical connection. As seen in FIG. 1, the proximal end 12 of test strip 10 includes a sample receiving location, such as a sample chamber 20 configured to receive a patient's fluid sample, as described above. The sample chamber 20 may be formed in part through a slot formed between a cover 22 and the underlying measuring electrodes formed on the base layer 16. The relative position of the measuring electrodes and the electrical strip contacts form a proximal electrode region 24 at one end of strip 10 and a distal strip contact region 26 at the other end.

The conductive pattern of the test strip 10 may be covered by a non-conductive resistive layer having a range of resistive values. The resistive values may be configured by the use of a range of materials having various resistive properties.

The resistance may be varied from strip to strip by using a different material with predetermined resistive properties on each strip. The resistance may be varied from strip lot to strip lot by using a different material with predetermined resistive properties for each strip lot. The resistance may also be varied from strip to strip or from strip lot to strip lot by using a combination of various materials having predetermined resistances. For example, a certain pattern of resistive material may be coated on a conductive region of a test strip. This pattern can be varied from strip to strip or from strip lot to strip lot to allow the test strip to have various characteristics when read by the test strip meter. The pattern can be varied by using one predetermined resistive material or using a combination of two or more resistive materials. Since the test strip may comprise a conductive layer and a resistive coating on top, the resistance of the sensed region of the test strip may be configured to fall anywhere between highly conductive (with no resistance) and non-conductive (with high resistance).

Figure 2:
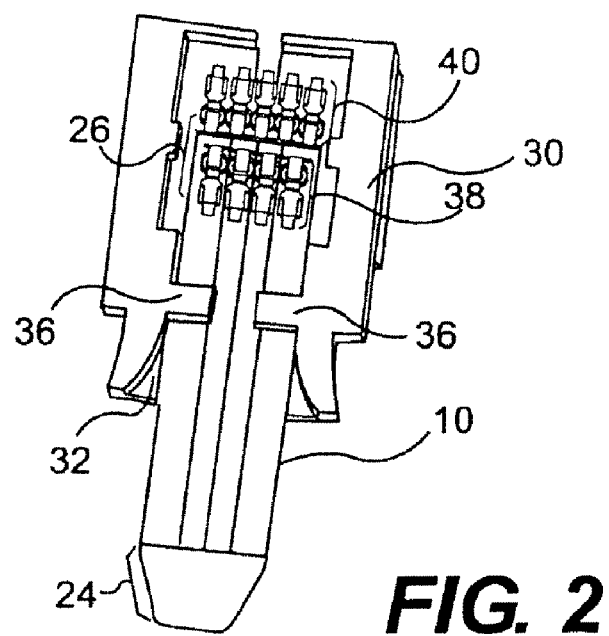
FIG. 2 is a top perspective view of a test strip inserted within a meter strip connector according to an embodiment consistent with the invention.

Referring to FIG. 2, a top perspective view of a test strip 10 inserted within a meter connector 30 is illustrated. As seen in FIG. 2, the strip 10 includes a proximal electrode region 24, which contains the sample chamber and measuring electrodes described above. The proximal electrode region 24 may be formed to have a particular shape in order to distinguish to the user, the end receiving a fluid sample from distal strip contact region 26. The meter connector 30 includes channel 32 extending out to a flared opening for receiving the test strip 10. The connector 30 may further include tangs 36 extending a predetermined height above the base of channel 32. The predetermined height of tangs 36 is selected to limit the extent, such as through a corresponding raised layer of test strip 10, to which a test strip 10 can be inserted into channel 32.

Figure 3:
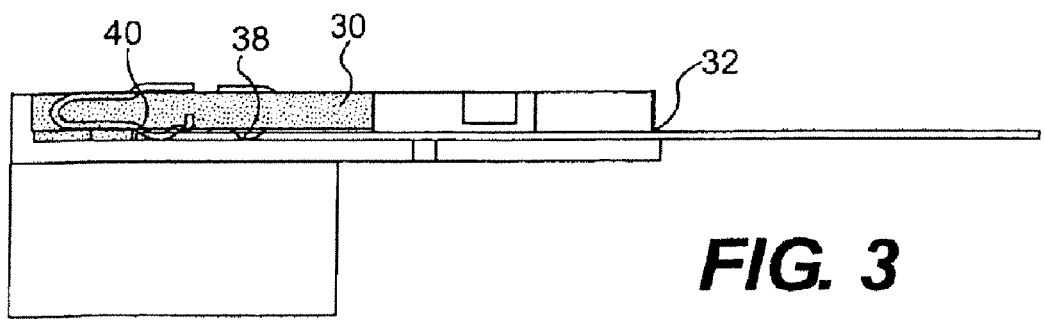
FIG. 3 is a general cross-sectional view of a test strip inserted within a meter strip connector according to an embodiment consistent with the invention.

The connector 30 further includes a first plurality of connector contacts 38, disposed closer to the proximal end of the connector 30, and a second plurality of connector contacts 40 disposed closer to the distal end of the connector 30. As illustrated, the test strip 10 is inserted into the flared opening with the distal strip contact region 26 extending first through the connector channel 32. With reference to FIG. 3, a general cross-sectional view of a test strip inserted within a meter strip connector 30 is illustrated. The channel 32 depicts a proximal row of connectors comprising a first plurality of connector contacts 38. In addition, the channel 32 houses a distal row of connectors comprising a second plurality of connector contacts 40. The connector contacts 38 and 40 make contact with distinct portions of the distal strip contact region 26, as will be described more fully below.

FIG. 3 is a general cross-sectional view of a test strip inserted within a meter strip connector according to an embodiment of the invention. The connector 30 contacts the test strip in one configuration. The connector contacts 38, 40 also make contact with the test strip in another configuration.

Figure 4A:
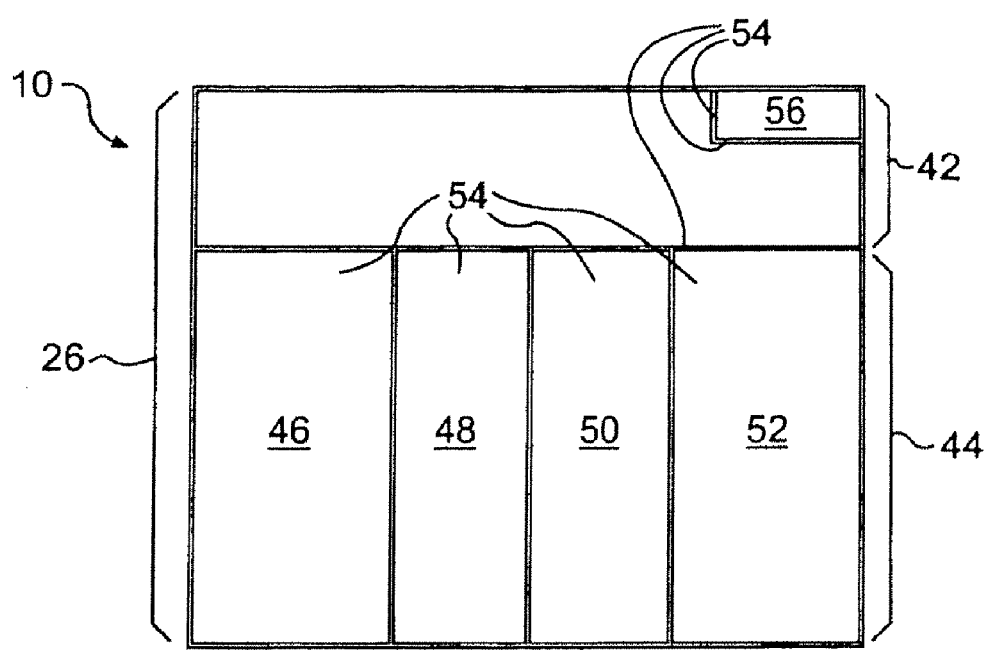
FIG. 4A is a top view of a distal portion of a test strip illustrating breaks dividing particular regions of the test strip connecting end according to an embodiment consistent with the invention.

FIG. 4A is a top view of a distal portion of a test strip 10 illustrating the distal strip contact region 26. The conductive pattern formed on base layer 16 extends along strip 10 to include the distal strip contact region 26. As illustrated in FIG. 4A, distal strip contact region 26 is divided to form two distinct conductive regions, 42 and 44 respectively. However, test strip 10 may comprise more than two distinct conductive regions. Conductive region 44 is divided into four columns forming a first plurality of electrical strip contacts, labeled 46, 48, 50, and 52 respectively. The first plurality of electrical strip contacts are electrically connected to the plurality of measuring electrodes at the distal end of the test strip 10 as explained above. It should be understood that the four contacts 46-52 are merely exemplary, and the system could include fewer or more electrical strip contacts corresponding to the number of measuring electrodes included in the system.

The first plurality of electrical strip contacts 46-52 are divided, for example, through breaks 54 formed through the underlying conductive pattern in the test strip 10. These breaks could be formed in the conductive pattern during printing, through a scribe process, laser ablated, or through a chemical/photo-etching type process. In addition, other processes of forming conductive breaks by removing a conductor in the test strip 10 may be used as would be apparent to one having ordinary skill in the art. An additional break 54 divides conductive region 44 from conductive region 42 within distal strip contact region 26, and a further break 54 separates the upper right-hand portion of distal strip contact region 26 to form a notch region 56, as will be described more fully in detail below.

Figure 4B:
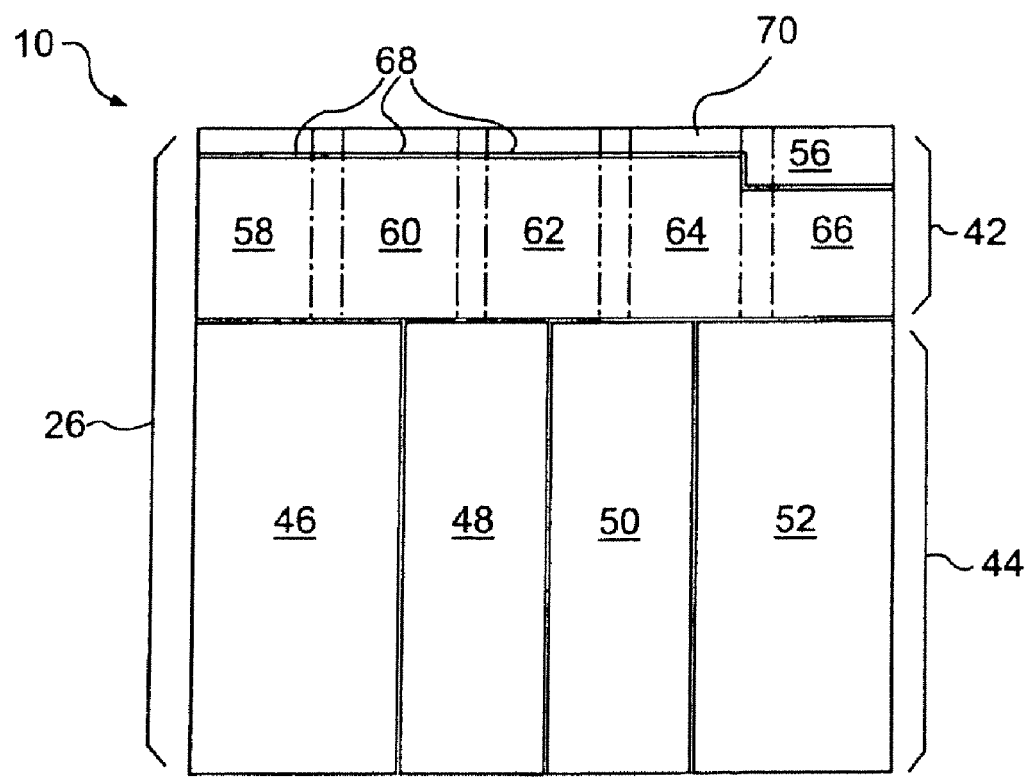
FIG. 4B is a top view of a distal portion of a test strip illustrating conductive regions forming electrical contacts according to an embodiment consistent with the invention.

FIG. 4B illustrates an additional view of the distal strip contact region 26. In FIG. 4B, conductive region 42, described above with regard to FIG. 4A, is divided into five distinct regions outlining a second plurality of electrical strip contacts forming contacting pads 58, 60, 62, 64, and 66 respectively. The second plurality of electrical strip contacts forming contacting pads 58, 60, 62, 64, and 66, can be divided through the same process used to divide the first plurality of electrical strip contacts, 46, 48, 50, and 52, described above. As noted above, the conductive pattern on base layer 16, which at least in part forms the electrical strip contacts, can be applied to the top side of the strip, the bottom side of the strip, or a combination of both. The contacting pads 58, 60, 62, 64, and 66 are configured to be operatively connected to the second plurality of connector contacts 40 within meter connector 30. Through this operative connection, the meter is presented with, and reads from the contacting pads, a particular code representing information signaling the meter to access data related to the underlying test strip 10. In addition, FIG. 4B depicts a further pattern of breaks 68, isolating an outermost distal connecting end 70 of the distal strip contact region 26.

Figure 4C:
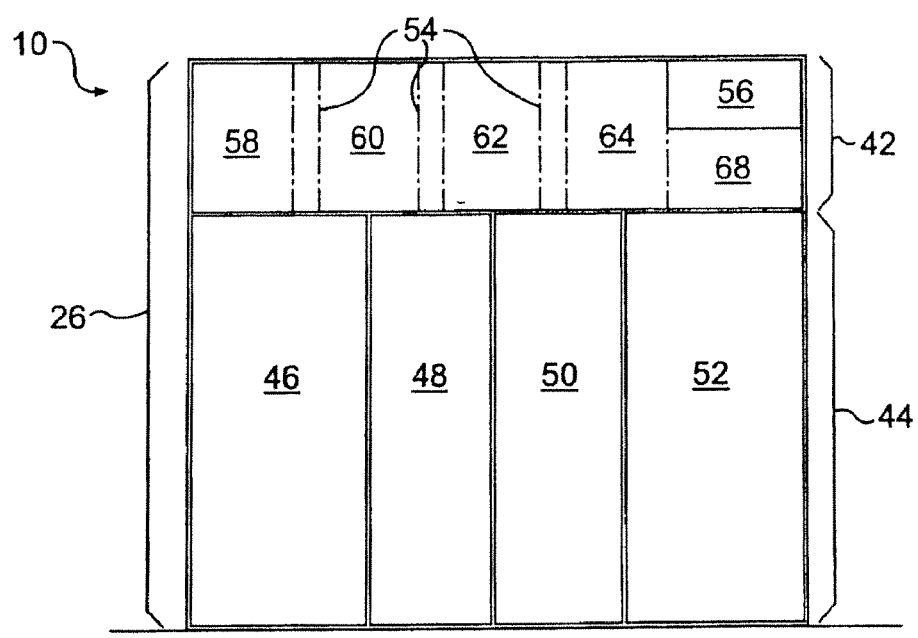
FIG. 4C is a top view of a distal portion of a test strip illustrating a particular arrangement for a plurality of electrical contacts according to an embodiment consistent with the invention.

FIG. 4C illustrates an additional view of the distal strip contact region 26. In FIG. 4C, the distal strip contact region 26 is depicted to include the first plurality of electrical strip contacts 46-52, the second plurality of electrical strip contacts forming contacting pads 58, 60, 62, 64, and 66, and the separated notch region 56. As noted, the above described conductive regions can all be formed as a result of breaks 54 within the underlying conductive pattern of test strip 10.

Figure 4D:
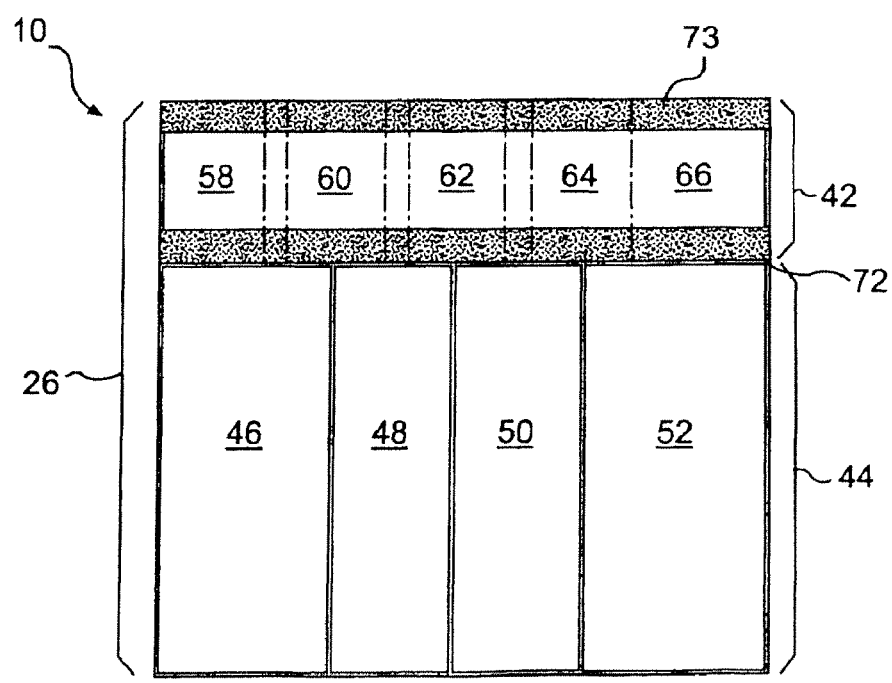
FIG. 4D is a top view of a distal portion of a test strip illustrating multiple insulators covering particular regions of the test strip connecting end according to an embodiment consistent with the invention.

FIG. 4D illustrates additional features of the distal strip contact region 26. A strip of non-conductive insulating ink 72 can provide further separation between conductive region 44 and conductive region 42 within distal strip contact region 26. The borders between the two regions can be printed with the insulating ink 72 in order to maintain distinct areas of conductivity (bordered by a distinct area of insulation) and to prevent scratching by meter connector contacts during the strip insertion process, which can adversely affect the desired conductivity of one of the strip contacts. The non-conductive insulating ink 72 can be administered, for example, through a screen printing process. Such screen printing of a dielectric insulation coating is advantageous in that it can be applied later on in the strip manufacturing process and in an easily programmable/reproducible pattern. The additional step of adding such an insulating coating can be less expensive and time consuming than methods requiring substrate ablation in some form. For example, ablating a substrate surface through a laser or chemical ablation process involves a time consuming process of precisely removing a particular pattern of preexisting material.

FIG. 4D illustrates that test strip 10 may include another strip of non-conductive insulating ink 73 formed at the distal end of the test strip 10. The strip of non-conductive insulating ink 73 provides a non-conductive region at the distal end of the strip 10. The strip 73 thereby prevents any meter connector contacts from creating an active conductive connection with any portion of contacting pads 58, 60, 62, 64, and 66 before the strip is fully inserted into the meter. Accordingly, strip 73 provides an additional feature for assuring a proper connection between the test strip 10 and the corresponding meter.

In any of the above embodiments, the conductive pattern may comprise a region having one or more predetermined electrical properties (e.g. resistance) per test strip. In another embodiment, the conductive pattern of a strip lot may comprise one or more predetermined resistances distinct from the corresponding predetermined resistances of the corresponding conductive pattern on another strip lot. This allows resistances to be different from strip lot to strip lot. The resistances may be varied by use of different materials or processes resulting in regions, e.g. contacts, with varying predetermined resistances.

The conductive pattern may be coated with a pattern of at least partially resistive material in order to provide different patterns that will determine different properties for the test strip. The pattern of resistive materials can be a pattern using one resistive material or a combination of two or more resistive materials to feature different resistive values and properties for the test strip.

Figure 5:
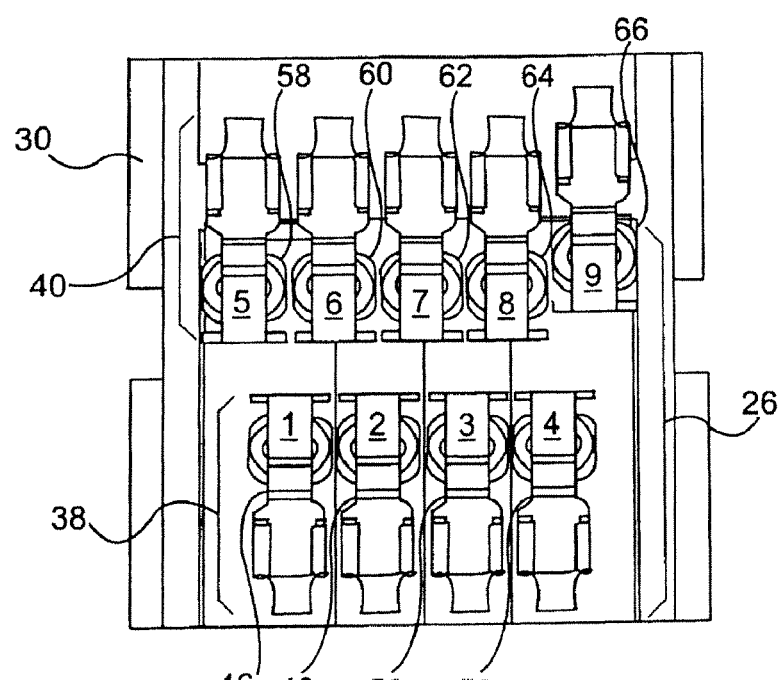
FIG. 5 is an expanded top view of a distal portion of a test strip inserted within a meter strip connector according to an embodiment consistent with the invention.

Referring to FIG. 5, meter strip connector 30 is illustrated receiving a distal strip contact region 26 of test strip 10. FIG. 5 depicts a first plurality of connector contacts 38, labeled 1-4 respectively, and a second plurality of connector contacts 40, labeled 5-9. The connector contacts 38 and 40 make contact with distinct portions of the distal strip contact region 26. In particular, upon proper insertion of the test strip 10 into connector 30, the electrical strip contacts 46-52, which form the first plurality of electrical strip contacts, are respectively electrically connected to the connector contacts 1-4, which form the first plurality of connector contacts 38. Similarly, the contacting pads 58, 60, 62, 64, and 66, which form the second plurality of electrical strip contacts, are respectively electrically connected to the connector contacts 5-9, which form the second plurality of connector contacts 40.

As seen in FIG. 5, the first plurality of connector contacts 38 are laterally staggered or offset, relative to the second plurality of connector contacts 40. Although the first and second plurality are illustrated as being in distinct rows and offset from each other, they need not be in distinct rows and can instead be offset in an additional manner, such as, for example, in distinct groups. Accordingly, as a test strip 10 is inserted into meter connector 30, the conductive signal provided by contacting pads 58-66 is unhindered by any scratches or scuffs that would otherwise result from first sliding contacting pads 58-66 under connector contacts 1-4 in order to reach their destination connection at connector contacts 5-9. Therefore, the staggered arrangement of connector contacts 38 relative to connector contacts 40 provides a more reliable connection. In addition, the application of strip 72 of non-conductive insulating ink (FIG. 4D) also assists in preventing the conductive coating from one of contacting pads 58-66 from being scratched and "plowed" away by the friction and interaction from the meter connector contacts 38. Accordingly, strip 72 of non-conductive insulating ink provides increased reliability of connector and contact conduction.

In one embodiment, the connection between contacting pad 66 and connector contact 9 establishes a common connection to ground (or a voltage source where the polarity is reversed), thereby completing an electric circuit, which includes the meter and at least a portion of conductive region 42. The completion of this circuit can perform a meter wake-up function, providing a signal to the meter to power up from low-power sleep mode. Therefore, as illustrated in FIG. 5, the connector contact 9 may be positioned proximally relative to the remaining contacts 5-8, in order to ensure that connectors 5-8 are in proper connecting position prior to the final closing/wake-up of the circuit through the connection of contacting pad 66 and connector contact 9. Furthermore, because the non-conductive insulating ink strip 73 (See FIG. 4D) can be formed at the distal end of the test strip 10 and also because a conducting substance can be removed from notch region 56 (See FIG. 4C), premature wake-up of the meter will be prevented.

In other words, during distal movement of test strip 10 within the connector channel 32, the common connection will not be established at the point connector contact 9 engages the extreme distal edge of test strip 10. Instead, common connection will be established only when the connector contact passes notch 56, and ink strip 73 if applied, and engages a conductive portion of contacting pad 66. Accordingly, the combination of a proximally positioned connector contact 9 and a non-conductive notch region 56 provides a more reliable connection between strip 10 and the meter.

As noted above, the contacting pads 58, 60, 62, 64, and 66 are configured to be operatively connected to the second plurality of connector contacts 40 within meter connector 30. Through this operative connection, the meter is presented with, and reads from the contacting pads, a particular code signaling the meter to access information related to a particular underlying test strip 10. The coded information may signal the meter to access data including, but not limited to, parameters indicating the particular test to be performed, parameters indicating connection to a test probe, parameters indicating connection to a check strip, calibration coefficients, temperature correction coefficients, pH level correction coefficients, hematocrit correction data, and data for recognizing a particular test strip brand.

Figure 6:
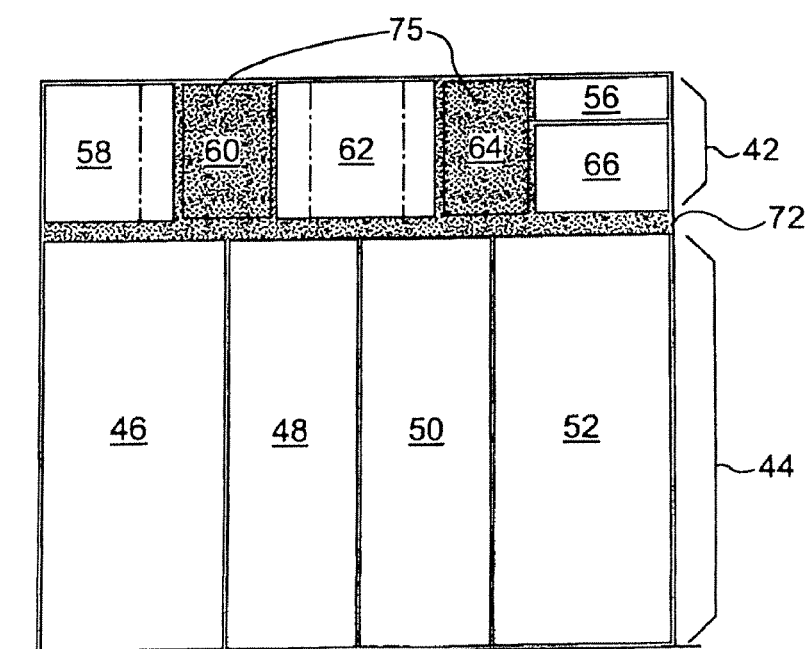
FIG. 6 is a top view of a distal portion of a test strip illustrating a plurality of electrical contacts forming a code according to an embodiment consistent with the invention.

One such code is illustrated in FIG. 6, where conductive contacting pads 60 and 64 are overprinted with an electrical insulting material, such as, for example, a non-conductive (insulating) ink layer 75. A non-conductive ink layer 75 significantly increases the impedance (and may even prevent the flow of electric current therealong) between the corresponding connector contacts (in this example, connector contacts 6 and 8) and the underlying strip portion at various predetermined contacting pads within the conductive region 42 of distal strip contact region 26. Just as described above, with regard to FIG. 4D, the use of non-conductive insulating ink 75 is particularly advantageous relative to other methods of altering the conductivity of a strip portion.

An exemplary insulating material includes, but is not limited to, VISTASPEC HB Black available from Aellora™ Digital of Keene, N.H. The VISTASPEC HB Black material is a hybrid UV-curable black-pigmented ink for use in elevated temperature piezo drop-on-demand ink jet arrays. This VISTASPEC ink is jetted at an elevated temperature, rapidly sets upon contact with the underlying substrate, and is then cured by UV radiation. The ink's properties include electrical insulation, resistance to abrasion from a meter's contacts, enhanced adhesion to an underlying conductive material, and beneficial visco-elastic characteristics. The material's visco-elastic characteristics minimize ink spreading on the underlying substrate. Furthermore, these visco-elastic characteristics enable this ink to be utilized with high print resolution piezo technology that enables accurate and precise patterning of the VISTASPEC ink onto the conductive electrode substrate. In addition, the visco-elastic characteristics of the VISTASPEC ink enables a sample as small as about an 80 picoliter drop to remain pinned at the location where it makes contact with the underlying substrate, thereby enabling precise pad sizes, positional accuracy, and precision of up to less than about 0.005 inches. As an example, printing of the insulating material can be accomplished through the use of a SureFire Model PE-600-10 single pass piezo drop-on-demand ink jet print engine, also available from Aellora™ Digital of Keene, N.H. As non-limiting examples, the above described ink jet print engine can utilize Nova and Galaxy model print heads available from Spectra Inc. of Lebanon, N.H. The above-mentioned examples are non-limiting as other types of ink jet print engines may be used in conjunction with other types of print heads known in the art.

Systems requiring the ablation of a substrate surface through a laser or chemical ablation process involves the time consuming process of precisely removing a particular pattern of preexisting material. Because coding of the strip occurs later in the assembly process than the ablation step, adding a non-conductive ink layer 75 to the contacting pads eliminates the tolerance issues that would result from reintroducing strips into a larger ablation process for coding. Such printing of a dielectric insulation coating is advantageous in that it can be applied later on in the strip manufacturing process and in an easily programmable/reproducible pattern. As a non-limiting example, the method of providing layer 75 to the underlying substrate can include the use of at least one registration datum along the underlying strip to ensure accurate formation of the layer 75 according to a particular desired pattern. For example, datums can be provided orthogonally (e.g. longitudinally and laterally) along a substrate where that can be mechanically or optically referenced by a printing apparatus to facilitate the formation of an accurate and reproducible pattern. Depending on the arrangement of the electrical strip contacts, the discrete portions of electrical insulating material forming each layer 75 can be applied to the top side of the strip, the bottom side of the strip, or a combination of both.

Upon connection of the contacting pads 58, 60, 62, 64, and 66 in FIG. 6 to the corresponding connector contacts 40, the meter will read a particular code based on the number, and pattern, of contacting pads overprinted with a non-conductive ink layer 75. In other words, the use of non-conductive ink layer 75, provides a switching network to be read by the meter. When an insulator is printed over one of the conductive surfaces of contacting pads 58, 60, 62, 64, and 66, it prevents the flow of electric current therealong and alters the conductive path between the contacting pad and connector contact (e.g. where no current flows). When no insulator is printed over the conductor, current flow is relatively unimpeded (a low impedance path).

Upon reading a particular code, an internal memory within the meter can access, through a stored microprocessor algorithm, specific calibration information (such as, for example, calibration coefficients) relating to the particular test strip. The meter can read the code through either an analog or digital method. In the analog mode, a preset resistive ladder is interconnected within the meter to the second plurality of connector contacts 40 (labeled 5-9 in FIG. 5) such that permutations of printed non-conductive ink can be correlated to a distinct lot code using a voltage drop, resistance, or current measurement. The analog method also can be simultaneously used as the auto-on/wake-up feature as long as each code has at least one pad free of non-conductive ink that can make a low impedance connection to wake the meter up by closing an open circuit. The analog voltage, resistance, or current level could be used to signal the meter to access any of the data referenced above particular to the underlying test strip.

Figure 7:
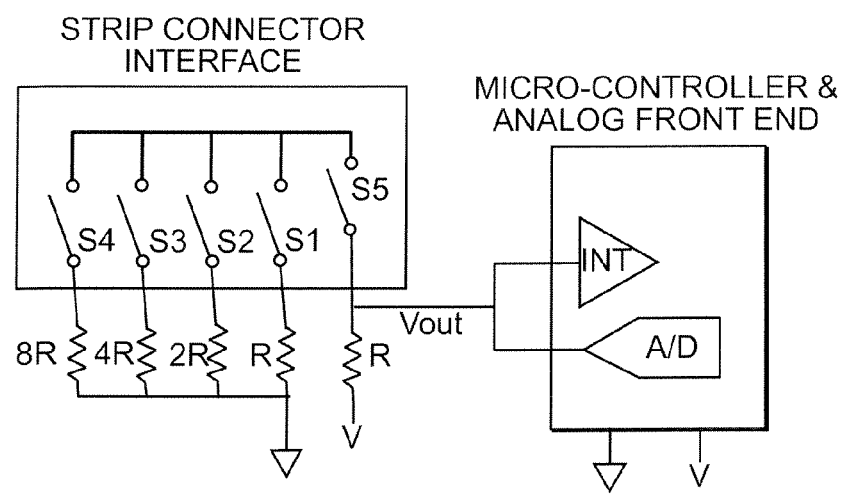
FIG. 7 is a simplified schematic diagram of the electrical connections between a meter and a plurality of electrical contacts of a test strip according to an embodiment consistent with the invention.

FIG. 7 depicts a schematic diagram of the electrical connections between a meter and contacting pads 58, 60, 62, 64, and 66 of a test strip according to an embodiment of the invention. Switch S5 of FIG. 7 provides the connection to a single voltage source V. Accordingly, switch S5, represents the required connection of contacting pad 66 and connector contact 9 in the analog code reading process. Switches S4-S1 schematically represent the connection between connector contacts 5-8 and contacting pads 58-64 of FIG. 5, respectively. When a non-conductive ink layer 75 is provided over one of the contacting pads 58, 60, 62, and 64, the corresponding switch, S4, S3, S2, or S1, will prevent the flow of electric current therealong upon physical engagement with a corresponding connector contact 5-8. Accordingly, a particular code will correspond to a particular switching configuration, in the switch network of FIG. 7. In another embodiment, a test strip and a meter may comprise more contacting pads and more corresponding switches.

As further seen in FIG. 7, each of switches S4-S1 close to add a distinct value of additional impedance to the closed circuit, by bridging the connection to a particular resistor. Therefore, through the application of Ohm's and Kirchhoff's laws, a circuit measurement at $V_{out}$ will provide distinct values based on the particular code presented by test strip 10. In an alternative embodiment, the direction of current flow can be reversed, if desired, by connecting switch S5 to common ground and instead connecting the resistor R to the single voltage source.

Figure 8:
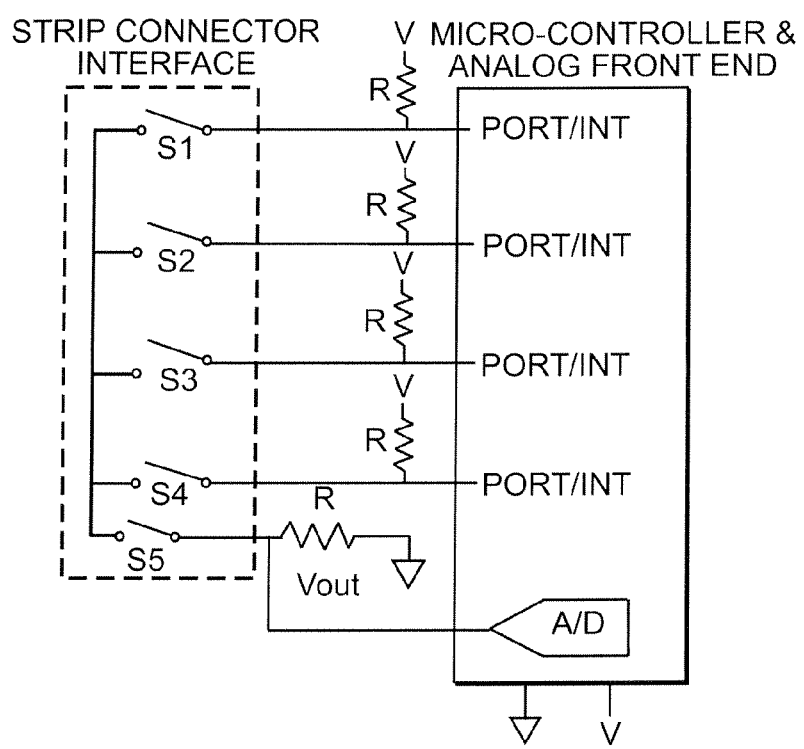
FIG. 8 is an alternative simplified schematic diagram of the electrical connections between a meter and a plurality of electrical contacts of a test strip according to an embodiment consistent with the invention.

In the digital mode, as schematically represented in FIG. 8, each contacting pad 58-66, would be read as an individual input, unlike the single input used by the analog method. For the digital method to be simultaneously used as an auto-on/wake-up feature, the inputs would need to be wire-orred together or connected to an interrupt controller of a microcontroller. Each code must have at least one pad free of non-conductive ink 75 such that a low impedance connection can be made to wake-up the meter's micro-controller.

Figure 9:
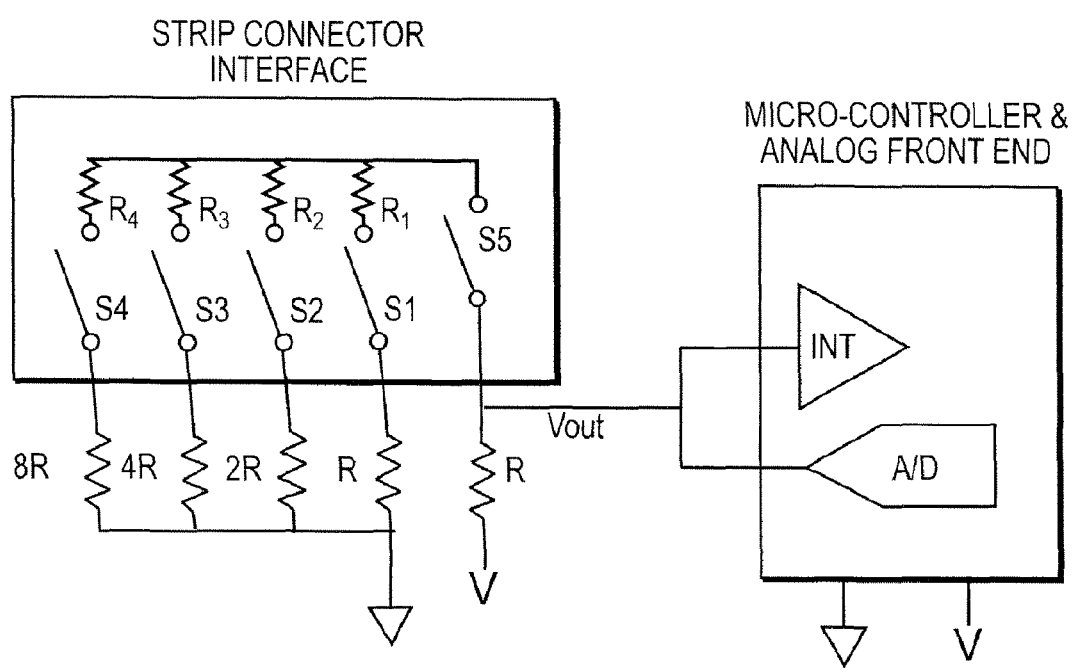
FIG. 9 is a simplified schematic diagram of the electrical connections between a meter and a plurality of electrical contacts of a test strip according to a further embodiment consistent with the invention.

FIG. 9 depicts another simplified schematic diagram of the electrical connections between a meter and contacting pads 58, 60, 62, 64, and 66 of a test strip according to a further embodiment of the invention. It is contemplated that the ink or coating could have a predetermined resistance, and that one or more of these inks or coating can be used to create a pattern resulting in a resistance. Switch S5 of FIG. 9 provides the connection to a single voltage source V. Accordingly, switch S5, represents the required connection of contacting pad 66 and connector contact 9 in the analog code reading process. Switches S4-S1 schematically represent the connection between connector contacts 5-8 and contacting pads 58-64 of FIG. 5, respectively, and also model the behavior of the system when a non-conductive, insulating ink layer 75 is provided over one of the contacting pads 58, 60, 62, and 64. In this case, when a conductor is coated with an insulative ink, the corresponding switch, S4, S3, S2, or S1, will be modeled as open and prevent the flow of electric current therealong upon physical engagement with a corresponding connector contact 5-8. As depicted, each branch of the test strip connected to the strip connector interface is further optionally provided with an ink or coating having a known resistance. The resulting pattern of resistances results in a total resistance signature for the strip, which can represent a code identifying the test strip.

Accordingly, a particular code will correspond to a particular switching configuration, in the switch network of FIG. 9. Different from FIG. 7, FIG. 9 depicts the test strip as having resistors R1 through R4 in series with switches S1 through S4, allowing for a different and additional combinations of resistive values than that provided by the circuit design of FIG. 7. In another embodiment, a test strip and a meter may comprise more contacting pads and more corresponding resistors and switches.

Non-conductive ink 75 with levels of high and low impedance produce a binary code yielding a code index based on the number of pads (P) implemented, where the number of codes is $N=2^P$. It is possible, however, for a code to comprise an arrangement where none of the electrical strip contacts are covered with electrical insulating material (a code with all logical "1"s, i.e. all conductors). The number of codes possible when integrated with an auto-on/wake-up feature, however, is reduced to $N=2^P-1$. In a system having an auto-on/wake-up feature, a code with all zeros (all insulators) is not an active code as it will not wake up the meter.

In another embodiment of the invention, the non-conductive ink 75 may produce a non-binary code yielding a code index resulting in the number of codes becoming $N=X^P$, where X may be greater than 2. This non-binary code may be possible by the use of various types of materials having predetermined resistance values, used alone or in combination with each other to provide resistance values between the resistance values of a code with all logical "1"s and a resistance value of a code with all logical "0"s. The number of codes possible when integrated with an auto-on/wake-up feature, however, is reduced to $N=X^P-1$, where X may be greater than 2.

When a strip 10 is inserted into the meter connector 30, one contact is closed and wakes up the meter by pulling the microcontroller's interrupt either high or low. The meter will then check the voltage out ($V_{out}$) to determine the test type and then read the code bits (S1, S2, S3, S4) to determine the code value. The code value selected can, for example, be associated with a stored set of coefficients in the meter's memory for use in a glucose mapping algorithm that is particularly correlated to the reagent applied to the measuring electrode region. This code can also be associated with other types of strip parameter information, such as those referenced above. It could also select different meter configuration options as well. The voltage drop across the series resistor R at Vout in FIG. 8 can be sensed, to determine if code values are within a predetermined range for use as a confirmation signal. This can also be used to determine strip identification (check strip, manufacturing probe, and different test type). The meter may comprise a multimeter or ohmmeter to detect resistance of the test strip.

In addition to providing either a high or low impedance level (through the application or absence of an insulating layer of non-conductive ink 75 over one of the contacting pads) a particular resistive element may be applied over a particular contacting pad. The resistive element introduces an increased level of impedance into a circuit that reduces (but does not necessarily prevents) the flow of electric current. Accordingly, the use of a specific resistive element over a particular contacting pad provides an intermediate level of resistance directly on the contacting pad of the test strip. When this intermediate level of resistance is connected to the meter through engagement with a corresponding meter connector contact, the meter can detect this "intermediate" level (e.g. through a circuit measurement of voltage drop by applying Ohm's and Kirchhoff's laws).

The resistive element over the contacting pad may comprise a predetermined resistance determined by a material used. A test strip may comprise one or more predetermined resistances through the use of varying materials used as resistive elements. The resistive element may also comprise a predetermined resistance that varies from strip lot to strip lot. This may be achieved through the use of various materials known in the art.

The resistance may be varied from strip to strip by using a different material with predetermined resistive properties on each strip. The resistance may be varied from strip lot to strip lot by using a different material with predetermined resistive properties for each strip lot. The resistance may also be varied from strip to strip or from strip lot to strip lot by using a combination of various materials having predetermined resistances. For example, a certain pattern of resistive material may be coated on the conductive layer of a test strip. This pattern can be varied from strip to strip or from strip lot to strip lot to allow the test strip to have various characteristics when read by the test strip meter. The pattern can be varied by using one predetermined resistive material or using a combination of two or more resistive materials. Since the test strip may comprise a conductive layer and a resistive coating on top, the resistance of the test strip may be configured to fall anywhere between highly conductive (with no resistance) and non-conductive (with high resistance).

The detection of such an intermediate level can alert the meter's processor to access an entire new set of code data relating to the particular test strip. In other words, providing a resistive element coating can be used to expand the number of codes available with a set number of contacting pads. For example, a strip may be formed with a particular code through a particular pattern of non-conducting insulating ink 75. When one of the conducting contacting pads is formed to include a particular resistive element, that same code represented by the pattern of non-conducting ink 75 now can be read by the meter to access an entirely different set of data. As an example, the contacting pad 66 of FIG. 6 (or any of the available contacting pads) could be formed to include a resistive element. As a non-limiting example, the resistive element could be provided in the form of a printed conductive ink. The thickness of the printed ink forming the resistive element, and resistivity of the ink composition, can be varied to achieve the desired resistance for a particular contacting pad. The additional information made available through this expansion of codes can include, but is not limited to, information related to hematocrit correction, information related to meter upgrades, and information related to the particular strip type. Accordingly, the use of such a resistive element can be used to expand the number of code configurations available with a set number of contacting pads.

It should be noted that the particular disclosed configurations of test strip 10, and in particular the configuration of connector contacts 38, 40 and the corresponding first and second plurality of electrical strip contacts, are merely exemplary, and different configurations could be formed without departing from the scope of the invention. For example, the underside of strip 10 can be formed to incorporate an additional number of contacting pads in order to increase the size (and thereby the amount of information) in the code index. The additional contacting pads on the underside of strip 10 could represent a third plurality of electrical strip contacts, thereby increasing the number of codes available. The number of available codes could thereby be expanded by applying an insulating coating to particular pads on the underside of strip 10 in addition to the coating of pads on the opposite side of the strip.

The incorporation of individualized code data within individual test strips provides numerous advantages in addition to those associated with accuracy of measurement. For example, with individual strip coding, a user no longer needs to manually enter the meter's lot code, thereby removing the possibility of user error for this critical step. Strip lot codes stored directly on individual test strips will also provide a means to ship mixed lots of strips in a single strip vial. In contrast, current technologies such as button/key coding require all strips (typically packaged in a vial including 50 strips from the same lot) in a vial to be from the same lot code.

Individual strip coatings representing particular codes also afford bulk packaging benefits. For example, mixed lot test strips and vials including different numbers of strips will be possible. Strips from various lots could be stored in a central location and packaged for sale without the time and expense of strips packaged from a single lot. Individual lot calibration codes stored on strips can also provide a means for varying a code across a single lot should a strip lot have variation from beginning to end or anywhere in between. Predetermined variations in manufacturing within a strip lot can be corrected by applying a continuously changing code across the lot, thereby solving yield problems and improving in-lot strip to strip variation. In addition, embedding lot codes on individual strips can be used to distinguish different types of test strips (e.g. glucose vs. ketone), check strips, or different manufacturing procedures, provide data for meter upgrades, and to correlate particular test strips for use only with a specific meter or meter type.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for measuring a body fluid constituent comprising:
   a test strip comprising:
      at least one electrically insulating layer with a proximal region and a distal region;
      a conductive pattern formed on the at least one insulating layer including at least one electrode disposed on the at least one insulating layer at the proximal region of the strip, electrical strip contacts disposed on the at least one insulating layer at a conductive region at the distal region of the test strip, and conductive traces electrically connecting the electrodes to at least some of the electrical strip contacts;
      a reagent layer contacting at least a portion of at least one electrode; and
      a machine-readable pattern formed on the at least one insulating layer and being readable to identify data particular to the test strip, the machine-readable pattern comprising a plurality of contacting pads with each contacting pad of the plurality of contacting pads having either a first or second predetermined electrical value, the first and second predetermined value being different from one another;
      wherein the contacting pads are disposed distal of the electrical strip contacts and are electrically separated from the electrical strip contacts, and
      wherein at least one of the contacting pads is a ground contacting pad configured to establish a common connection to an electrical ground, the ground contacting pad including a grounding portion to establish the connection to the electrical ground and a notch portion distal to and electrically separated from the grounding portion, wherein a distal edge of the grounding portion of the ground contacting pad is proximal to distal edges of the remaining contacting pads; and
   a diagnostic meter comprising:
      a connector comprising a channel having a proximal end and a distal end configured to receive the test strip; a first plurality of connector contacts and a second plurality of connector contacts disposed in the channel, the first plurality of connector contacts and the second plurality of connector contacts being positioned in the channel to contact the electrical strip contacts located in distinct portions of the contact region of the test strip, and a microprocessor operable with a decoder for decoding a resistance of the electrical strip contacts as information.

2. The system of claim 1, wherein the first plurality of connector contacts are positioned in the channel to contact the electrical strip contacts and the second plurality of connector contacts are positioned in the channel distally of the first plurality of the connector contacts to contact the contacting pads.

3. The system of claim 2, wherein the second plurality of connector contacts includes a grounding connector contact configured to contact a grounding contacting pad of the contacting pad, wherein a proximal edge of the grounding connector contact is positioned distally relative to proximal edges of the remaining connector contacts of the second plurality of connector contacts.

4. The system of claim 3, wherein, when the test strip is inserted into the channel from the proximal end toward the distal end, the grounding connector contacts the grounding contacting pad to activate a completion of a circuit to wake-up the meter by providing a signal to power up the meter from a low-power sleep mode.

5. The system of claim 1, wherein the connector contacts of the first plurality of connector contacts are arranged in a first row and the connector contacts of the second plurality of connector contacts are arranged in a second row distal to the first row.

6. The system of claim 1, wherein the first plurality of connector contacts are offset laterally relative to the second plurality of connector contacts.

7. The system of claim 1, wherein the material disposed over the at least one of the contacting pads is an electrically insulating material.

8. The system of claim 1, wherein the contacting pads have a predetermined electrical property of a first value and the material disposed over the at least one contacting pad changes the electrical property of the at least one contacting pad to a second value different from the first value.

9. The system of claim 8, wherein the second value is a non-zero value.

10. A method of making a plurality of test strips, the method comprising:
    forming a plurality of test strip structures on one sheet, each of said test strip structures including:
    (a) a sample chamber;
    (b) an electrically insulating layer with a proximal region and a distal region;
    (c) a conductive pattern comprising including a plurality of electrodes formed on said sheet, and a plurality of electrical strip contacts formed on said sheet, a portion of which are electrically connected to said plurality of electrodes;
    (d) a set of electrical strip contacts individually electrically isolated to form a discrete set of contacting pads formed on said sheet distally of and electrically isolated from said plurality of electrodes, each contacting pad of the set of contacting pads having either a first or second predetermined electrical value, the first and second predetermined value being different from one another, the first and second predetermined electrical values associated with the contacting pads forming a machine-readable pattern readable to identify data particular to the test strip; and
    wherein at least one of the contacting pads is a ground contacting pad configured to establish a common connection to an electrical ground, the ground contacting pad including a grounding portion to establish the connection to the electrical ground and a notch portion distal to and electrically separated from the grounding portion, wherein a distal edge of the grounding portion of the ground contacting pad is proximal to distal edges of the remaining contacting pads,
    separating said test strip structures into said plurality of test strips.

11. The method of making a plurality of test strips of claim 10, wherein the predetermined electrical values are a resistance.

12. The method of making a plurality of test strips of claim 10, wherein the predetermined electrical value of the at least one contact varies from strip lot to strip lot.

13. A test strip for measuring a body fluid constituent comprising:
    at least one electrically insulating layer with a proximal region and a distal region;
    a conductive pattern formed on the at least one insulating layer including at least one electrode disposed on the at least one insulating layer at the proximal region of the strip, electrical strip contacts disposed on the at least one insulating layer at a conductive region at the distal region of the test strip, and conductive traces electrically connecting the electrodes to at least some of the electrical strip contacts;
    a reagent layer contacting at least a portion of at least one electrode; and
    a machine-readable pattern formed on the at least one insulating layer and being readable to identify data particular to the test strip, the machine-readable pattern comprising a plurality of contacting pads with each contacting pad of the plurality of contacting pads having either a first or second predetermined electrical value, the first and second predetermined value being different from one another;
    wherein the contacting pads are disposed distal of the electrical strip contacts and are electrically separated from the electrical strip contacts, and
    wherein at least one of the contacting pads is a ground contacting pad configured to establish a common connection to an electrical ground, the ground contacting pad including a grounding portion to establish the connection to the electrical ground and a notch portion distal to and electrically separated from the grounding portion, wherein a distal edge of the grounding portion of the ground contacting pad is proximal to distal edges of the remaining contacting pads.

* * * * *